(12) United States Patent
Maeda et al.

(10) Patent No.: US 6,867,705 B2
(45) Date of Patent: Mar. 15, 2005

(54) REMOTE CONTROLLER FOR TELEVISION HAVING A FUNCTION OF MEASURING BODY FAT AND TELEVISION RECEIVER WITH THE SAME

(75) Inventors: Osamu Maeda, Daito (JP); Katsuhiro Morisada, Daito (JP); Shinji Yoshida, Daito (JP)

(73) Assignee: Funai Electric Co., Ltd., Daito (JP)

(*) Notice: Subject to any disclaimer, the term of this patent is extended or adjusted under 35 U.S.C. 154(b) by 271 days.

(21) Appl. No.: 10/282,258

(22) Filed: Oct. 29, 2002

(65) Prior Publication Data

US 2003/0090389 A1 May 15, 2003

(30) Foreign Application Priority Data

Oct. 29, 2001 (JP) ............................................ 2001-7046
Nov. 7, 2001 (JP) ............................................ 2001-7292

(51) Int. Cl.[7] ........................ G08C 19/00; G08C 19/12; H04L 17/02
(52) U.S. Cl. .................... 340/825.72; 341/176
(58) Field of Search ....................... 340/825.71, 825.72; 341/176; 348/134; 324/303; 600/547

(56) References Cited

U.S. PATENT DOCUMENTS 5,372,141 A * 12/1994 Gallup et al. ............... 600/547

FOREIGN PATENT DOCUMENTS

| JP | 07-059022 | 3/1995 |
|---|---|---|
| JP | 07-131775 | 5/1995 |
| JP | 10-014898 | 1/1998 |
| JP | 11-113873 | 4/1999 |
| JP | 2000-171288 | 6/2000 |
| JP | 2001-000410 | 1/2001 |
| JP | 2001-094898 | 4/2001 |
| JP | 2001-212098 | 8/2001 |

* cited by examiner

Primary Examiner—Michael Horabik
Assistant Examiner—Scott Au
(74) Attorney, Agent, or Firm—Crowell & Moring LLP (57) ABSTRACT

A remote controller for a television having a function of measuring a body fat includes a physical data setting section for registering a physical data including the weight and the height of a user and an impedance measuring circuit for measuring the impedance across the body to determine the body fat of the user. For determining the body fat of a user to be examined, the body fat meter equipped television remote controller registers the physical data including the weight and the height of the user, measures the impedance across the body of the user, and transmits to a television receiver a body fat measurement signal which carries the physical data and the impedance measurement. The television receiver calculates the body fat of the user from the physical data and the impedance measurement carried on the body fat measurement signal and displays a resultant calculation of the body fat on its display provided for displaying images of the existing television broadcasting.

14 Claims, 10 Drawing Sheets

REMOTE CONTROLLER FOR TELEVISION HAVING A FUNCTION OF MEASURING BODY FAT AND TELEVISION RECEIVER WITH THE SAME

BACKGROUND OF THE INVENTION

The present invention relates to a remote controller for a television having a function of measuring a body fat and a television receiver where the body fat of a user can be measured with the use of a remote controller provided for selecting a desired channel of the existing television broadcasting service or the video recording system.

In general, body fat meters have been known for measuring the rate or amount of body fat of a human body through feeding a small current across the body. Such body fat meters are commonly designed for measuring the impedance across the body of a user to be examined by a four-electrodes method and calculating the rate or amount of body fat of the user from a measurement of the impedance and the physical data including the weight, the height, the sex, and the age of the user. The body fat meters are classified into one type of measurement with the electrodes gripped directly by the hands of the user and another type of measurement with the electrodes on which the feet of the user are directly placed.

Most of the conventional body fat meters are commercially available as single-purpose products and some may be installed in bathroom scales or bathtubs. However, there are no such body fat meter equipped household appliances which are daily used and ready to hand.

A particular type of television receivers is also known which can be used as a lighting appliance when its CRT (Cathode Ray Tube) is controlled to illuminate in a single color by a remote controller provided for switching on and off the television receiver, selecting a desired channel of the TV broadcasting service, and controlling the audio and video settings (as disclosed, for example, in Japanese Patent Laid-open Publication No. 2001-94898). Alternatively, a CATV (Cable Television) receiver with a remote controller for automatically determining the code of an electric appliance currently connected is known where the maker code of an electric appliance such as a VTR (Video Tape Recorder) to be connected is judged from the blue back signal, white back signal, and black burst signal which are received from the video output of the VTR (as disclosed, for example, Japanese Patent Laid-open Publication No. HEI 7-131775).

Also known is a health management system arranged where the weight and the body fat of a user are measured by its measuring unit and their measurements are transferred in the form of an infrared ray signal to its display unit for display (as disclosed, for example, in Japanese Patent Laid-open Publication No. 2000-171288). A similar type of television receiver is provided where a recipe of cooking and its food materials are registered using its remote controller and their calories are calculated in its microcomputer and then displayed on its CRT screen (as disclosed, for example, Japanese Patent Laid-open Publication No. HEI 7-59022). A human body electric impedance meter is provided which has a microcomputer arranged in one-chip IC (Integrated Circuit) form for conducting various functions including the measurement of the impedance across a human body (as disclosed, for example, in Japanese Patent Laid-open Publication No. 2001-212098).

Another human body electric impedance meter is known which is minimized in the adverse effect of breathing and pulses (as disclosed, for example, in Japanese Patent Laid-open Publication No. HEI 10-14898). A body fat meter is provided which is less susceptible to variations in the impedance when the measurement electrodes are in direct contact with the human body (as disclosed, for example, in Japanese Patent Laid-open Publication No. HEI 11-113873). A further human body impedance meter is provided which is minimized in the adverse effect of environmental conditions including the temperature (as disclosed, for example, in Japanese Patent Laid-open Publication No. 2001-410).

However, as most of the conventional body fat meters are commercially available as single-purpose products, they are rarely combined with common household appliances which are daily used and ready to hand. Some may be installed in bathroom scales or bathtubs which are not handy and thus unfavorable for easily measuring the body fat of a user when desired. It is rather necessary for measuring the body fat of any user when desired to purchase a body fat meter of the single-purpose type. Accordingly, this will force the user to increase the expenditure.

For compensation, a scheme has been developed that the function of measuring the body fat of a user is installed in a common remote controller for a television receiver which is always ready to hand at every home. However, such a common remote controller has a microcomputer arranged of substantially a 4-bit, 1 Kbyte ROM which is too small to conduct all the functions of measuring the impedance across the body of a user, calculating the body fat of the user from a measurement of the impedance, and displaying a calculation of the body fat. When the microcomputer of the remote controller is desired for conducting all the functions, it has to be implemented by at least an 8-bit, 4 Kbyte ROM which is off course expensive.

The foregoing drawback will hardly be eliminated by the teaching of the prior art disclosed in the publication No. 2001-94898 or No. HEI 7-131775. Equally, each of the prior arts disclosed in the publication Nos. 2000-171288, HEI 7-59022, 2001-212098, HEI 10-14898, HEI 11-113873, and 2001-410 fails to eliminate the foregoing drawback.

SUMMARY OF THE INVENTION

The present invention has been developed for eliminating the foregoing drawback and its object is to provide a body fat meter equipped remote controller for a television which has a function of measuring the body fat of a user to be examined and a body fat meter equipped television receiver with such a remote controller while is minimized in the cost up for having the body fat measuring function, whereby the user can be free from purchasing a single-purpose body fat meter thus declining its expenditure while its body fat is easily measured at any desired time.

According to an aspect of the present invention, a remote controller for a television with a function of measuring a body fat having a transmitter which transmits a select signal for selecting a desired receiving/recording channel of television broadcasting to a television receiver and a control section which controls actions of each section of the remote controller, comprises: a physical data setting section which is operated by a user for registering physical data including a weight and a height of the user; an electrode section including a pair of current electrodes which feed a current across the body of the user through direct contact with the body and a pair of measurement electrodes which detect an electric signal generated by the current being fed across the body of the user; and an impedance measuring circuit which feeds the current between the current electrodes of the electrode section and measures an impedance across the body of the user to determine a body fat of the user from the electric signal detected by the measurement electrodes, wherein the transmitter is controlled by the control section to transmit to the television receiver a body fat measurement signal which carries the physical data registered by the physical data setting section and the impedance measured by the impedance measuring circuit so that the body fat of the user can be calculated in the television receiver.

The remote controller for a television of the present invention can measure the body fat of a user to be examined while selecting a desired receiving/recording channel of television broadcasting. For measurement of the body fat, the remote controller is operated to register the physical data including the weight and the height of the user and detect the impedance across the body of the user. As the physical data and the impedance measurement have been transmitted from the remote controller to the television receiver, the body fat of the user is calculated from the physical data and the impedance measurement and then displayed by the television receiver. Since the remote controller for a television is capable of measuring the body fat of any user, it is unnecessary to purchase a single-purpose body fat meter separately of the television receiver. Accordingly, the expenditure of the user can be minimized. Also, the remote controller is ready to hand at every home and can easily be used for measuring the body fat. While the physical data including the weight and the height of the user are registered and the impedance across the body of the user is measured by the remote controller, the calculation of the body fat of the user from the physical data and the impedance measurement is conducted and displayed by a television receiver which is higher in the electrical performance. As the result, the remote controller can be minimized in the cost of production without trading off its performance.

DETAILED DESCRIPTION OF THE PREFERRED EMBODIMENTS

Figure 1:
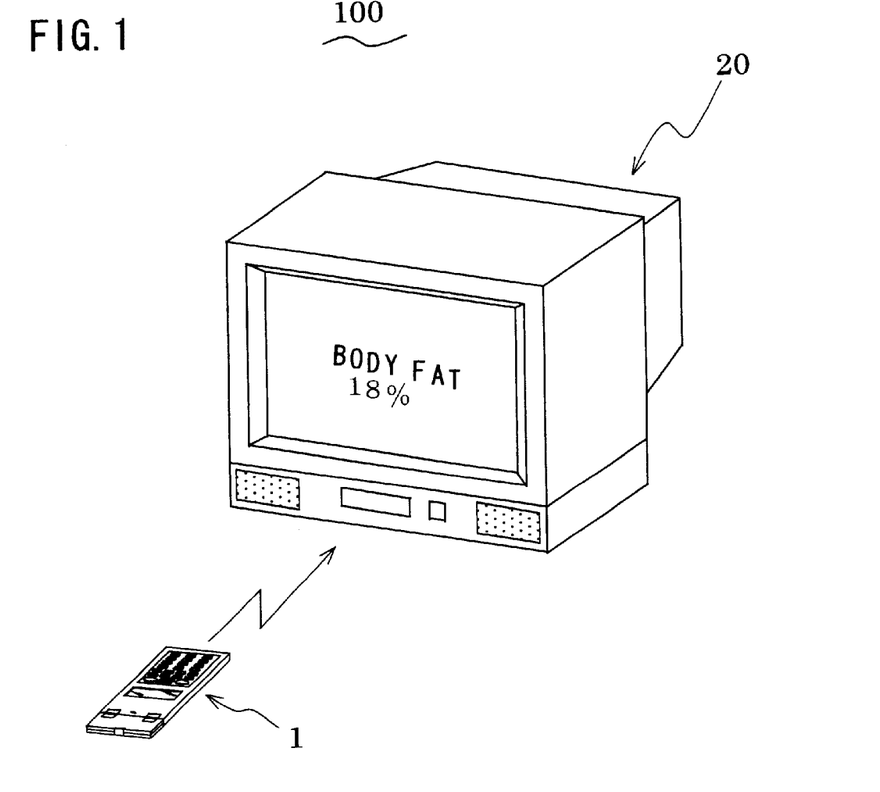
FIG. 1 is a perspective view of a body fat meter equipped television receiver showing a first embodiment of the present invention.

Some embodiments of the present invention will be described in more detail referring to the relevant drawings. FIG. 1 illustrates a television receiver equipped with a body fat meter according to a first embodiment of the present invention. The body fat meter equipped television receiver denoted by 100 is arranged for measuring and displaying the body fat of a user while receiving a television signal and reproducing its video and audio data and comprises a remote controller 1 and a main television unit 20 operated with the remote controller 1.

The remote controller 1 is provided for registering the physical data including the weight, the height, the sex, and the age of a user and measuring the impedance across the body of the user to determine the body fat of the user while selecting a desired channel of the existing television broadcasting service. In particular, the physical data and the impedance across the body of the user as well as the channel selection signal are transmitted to the main television unit 20 in the form of infrared ray signals. When receiving the infrared ray signals, the main television unit 20 reproduces video and audio data from the television broadcasting signal of the selected channel and calculates the body fat of the user from the impedance measured by and the physical data registered through the remote controller 1 and displays its calculation.

Figure 2A:
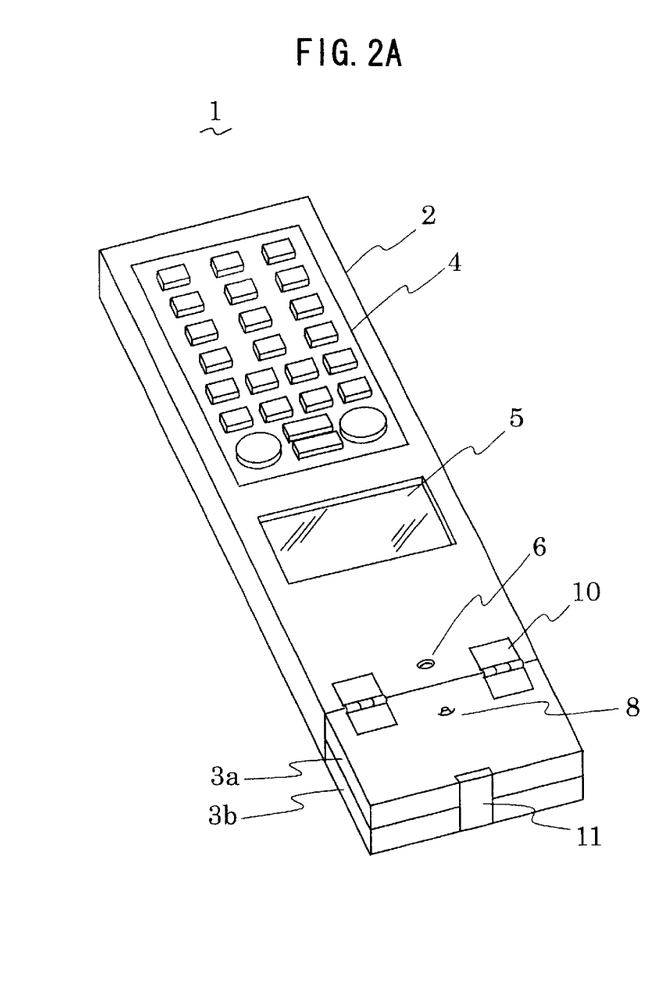
FIGS. 2A and 2B are perspective views of a remote controller for the television receiver of the first embodiment.
Figure 2B:
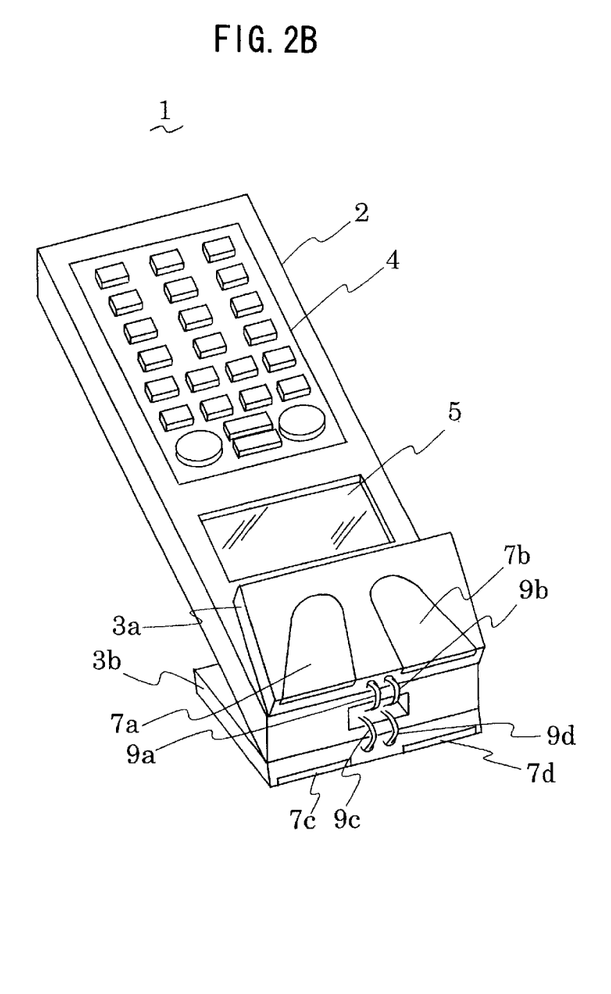

FIGS. 2A and 2B illustrate a remote controller 1 for the body fat meter equipped television receiver 100 of the embodiment. The remote controller 1 comprises a main unit 2 and a pair of openable sections 3a and 3b. The main unit 2 includes a keyboard (physical data setting section) 4, a liquid crystal display 5, and a measurement switch 6. The openable section 3a has a projection 8 provided on the outer side thereof and a pair of current electrodes 7a and 7b provided on the inner side thereof for feeding a current to measure the impedance across the body of a user. The openable section 3b has a pair of measurement electrodes 7c and 7d provided on the inner side thereof for measuring a voltage level to determine the impedance in the body while the current is fed across the body of the user by the current electrodes 7a and 7b. The current electrodes 7a and 7b and the measurement electrodes 7c and 7d are electrically connected to the main unit 2 by electrical cables 9a, 9b, 9c, and 9d respectively.

The openable sections 3a and 3b are located on this side of the remote controller 1 when it is in use and joined by hinges 10 to the main unit 2 for opening and closing. The openable sections 3a and 3b remain urged by spring means, not shown, for opening towards the upper and the lower respectively and closed together with a stopper 11 (See FIG. 2A). When the stopper 11 is unlocked, the two openable sections 3a and 3b are turned to their half open state by the yielding force of the spring means (FIG. 2B). As the openable section 3a is shifted from the half open state to the fully open state, its projection 8 presses against the measurement switch 6 on the main unit 2. With the two openable sections 3a and 3b remaining open, the current electrodes 7a and 7b and the measurement electrodes 7c and 7d are exposed at this side of the remote controller 1 when it is in use.

When the remote controller 1 is used for not measuring the body fat, its two openable sections 3a and 3b remain closed with the current electrodes 7a and 7b and the measurement electrodes 7c and 7d not exposed. For measuring the body fat, the stopper 11 is unlocked to open the two openable sections 3a and 3b. This allows the current electrodes 7a and 7b and the measurement electrodes 7c and 7d to be exposed for starting the measurement of the impedance across the body. More particularly, while the current electrode 7a and the measurement electrode 7c are held directly by the fingers of one hand (at the left) of the user, the current electrode 7b and the measurement electrode 7d are held directly by the fingers of the other hand (at the right). As the two openable sections 3a and 3b remain at their fully open state, the measurement switch 6 on the main unit 2 is turned on by the pressing action of the projection 8 of the openable section 3a for feeding a current across the body of the user by the current electrodes 7a and 7b. As the result, the impedance across the body of the user can be measured.

Figure 3:
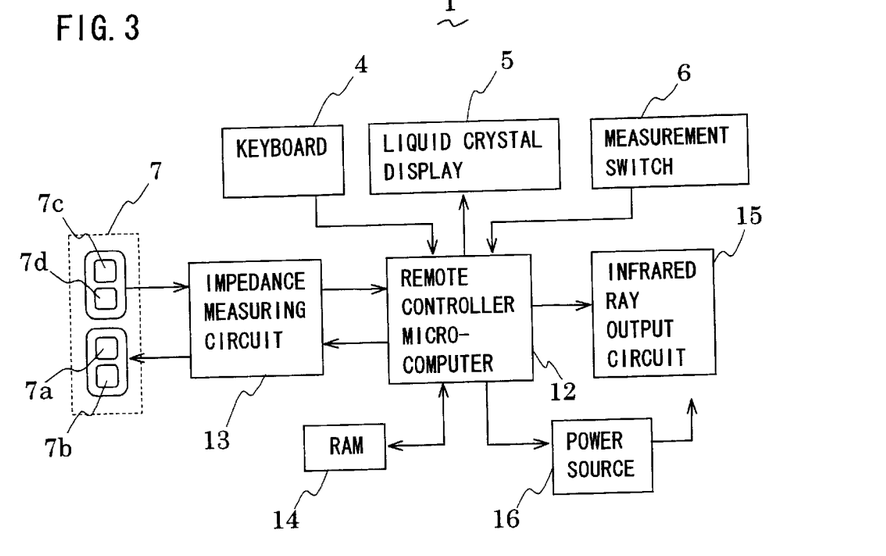
FIG. 3 is an electrical block diagram of the remote controller for the television receiver.

FIG. 3 is an electrical block diagram of the remote controller 1. The remote controller 1 includes a remote controller microcomputer (control section) 12 for controlling the actions of the remote controller 1. The remote controller microcomputer 12 is electrically connected to an impedance measuring circuit 13, a RAM 14, an infrared ray output circuit (transmitter) 15, and a power source 16 as well as the keyboard 4, the liquid crystal display 5, and the measurement switch 6. The impedance measuring circuit 13 is also connected to an electrode section 7 which consists mainly of the current electrodes 7a and 7b and the measurement electrodes 7c and 7d.

The keyboard 4 conducts switching between a TV control mode for selecting a desired channel of the existing TV broadcasting service and a body fat measurement mode for measuring the body fat of a user. In the TV control mode, the action is carried out for selecting a desired TV channel. In the body fat measurement mode, its relevant actions including the entry of the physical data of the user including the weight, the height, the sex, and the age and the display of measurements of the body fat can be carried out. When the entry actions are conducted at the keyboard 4, their corresponding signals are transferred to the remote controller microcomputer 12.

The liquid crystal display 5 is controlled by the remote controller microcomputer 12 for displaying the physical data of the user including the weight, the height, the sex, and the age received from the keyboard 4 and the other information. As the electrode section 7 consists mainly of the current electrodes 7a and 7b and the measurement electrodes 7c and 7d, the impedance across the body of the user can be measured by the user touching at one hand the current electrode 7a and the measurement electrode 7c and at the other hand the current electrode 7b and the measurement electrode 7d.

The measurement switch 6 is turned on when pressed down with the projection 8 and its ON signal is received by the remote controller microcomputer 12. The impedance measuring circuit 13 is controlled by the remote controller microcomputer 12 for feeding a current between the current electrodes 7a and 7b through the body of the user and measuring the voltage level between the measurement electrodes 7c and 7d to determine the impedance across the body of the user. The impedance determined by the impedance measuring circuit 13 is then transferred to the remote controller microcomputer 12.

The RAM 14 is controlled by the remote controller microcomputer 12 for saving the physical data including the weight, the height, the sex, and the age of the user entered from the keyboard 4 and the impedance determined by the impedance measuring circuit 13. The infrared ray output circuit 15 is controlled by the remote controller microcomputer 12 for transmitting select signals of the desired TV channels and measurement signals of the impedance and the physical data including the weight, the height, the sex, and the age in the form of infrared ray signals to the main television unit 20. The power source 16 supplies each unit with power.

Figure 4:
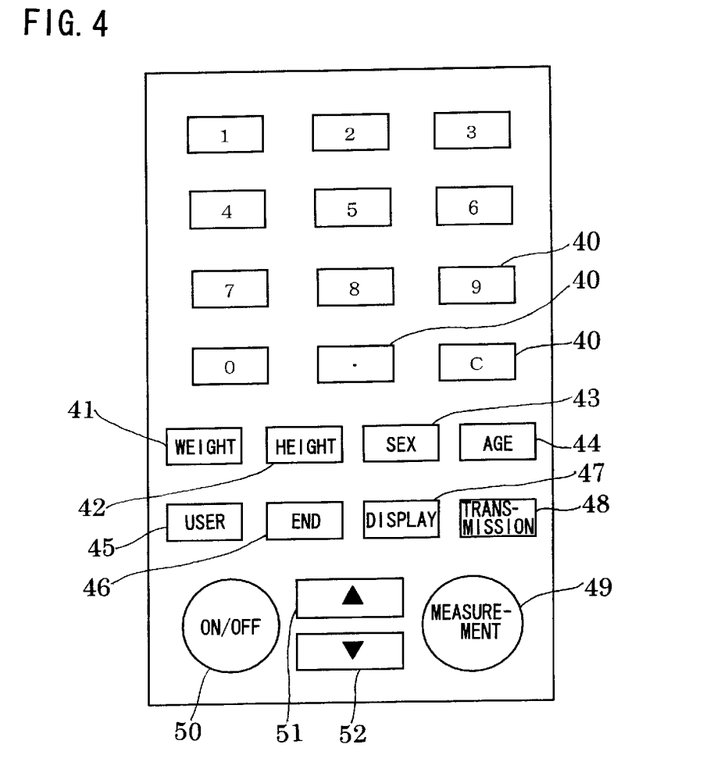
FIG. 4 is a view of a keyboard of the remote controller for the television receiver.

As shown in FIG. 4, the keyboard 4 includes a set of numerical entry keys 40, a weight entry key 41, a height entry key 42, a sex entry key 43, an age entry key 44, a user selector key 45, an end key 46, a display selector key 47, a transmission key 48, and a measurement key (body fat measurement key) 49. The keyboard 4 also includes a power on key 50 for turning the main television unit 20 on and off and a couple of sound keys 51 and 52 for adjusting the sound level of a speaker 28 in the main television unit 20.

The measurement key 49 is actuated for shifting from the TV control mode to the body fat measurement mode. The end key 46 is actuated for stopping the body fat measurement mode and returning back to the TV control mode. The numerical entry keys 40 are actuated for selecting a desired channel of the TV broadcasting service and entering the physical data of the user including the weight, the height, the sex, and the age. The physical data of the user are registered in the body fat measurement mode by pressing any of the weight entry key 41, the height entry key 42, the sex entry key 43, and the age entry key 44 and entering its corresponding number with the numerical keys 40. The user selector key 45 is actuated for determining the user to be measured for its body fat. The display selector key 47 is used for selecting the type of display of a measurement of the body fat on the main television unit 20. The transmission key 48 is actuated for transmitting the measured impedance and the physical data including the weight, the height, the sex, and the age of the user to the main television unit 20.

When the measurement key 49 of the keyboard 4 is turned on, the remote controller microcomputer 12 switches from the TV control mode to the body fat measurement mode. When the end key 46 of the keyboard 4 is turned on, the microcomputer 12 directs the infrared ray output circuit 15 to transmit an end signal indicating the end of the body fat measurement mode to the main television unit 20 and switches from the body fat measurement mode to the TV control mode. In the TV control mode, the remote controller microcomputer 12 allows the keyboard 4 to enter a desired channel of the TV broadcasting service. As the desired channel is selected by the action of the keyboard 4, its signal is released from the infrared ray output circuit 15. When the body fat measurement mode is selected, the remote controller microcomputer 12 allows the keyboard 4 to register the physical data including the weight, the height, the sex, and the age of the user and the display 5 to display a measurement of the body fat.

When having been registered through the keyboard 4 in the body fat measurement mode, the physical data including the weight, the height, the sex, and the age of the user are saved into the RAM 14 by the action of the remote controller microcomputer 12. Upon receiving the start signal from the measurement switch 6, the remote controller microcomputer 12 supplies the measuring circuit 13 with a command for starting the feeding of a current between the two current electrodes 7a and 7b of the electrode section 7. This permits the measuring circuit 13 to start measuring the impedance across the body of the user. After the measurement of the impedance, the remote controller microcomputer 12 saves a measurement of the impedance into the RAM 14 and simultaneously drives the infrared ray output circuit 15 to transmit the body fat measurement signal carrying the impedance and its corresponding physical data to the main television unit 20. The body fat measurement signal also acts as an ON signal for turning the power source of the main television unit 20 on.

When the transmission key 48 of the keyboard 4 is switched on in the body fat measurement mode, the remote controller microcomputer 12 transmits the body fat measurement signal carrying the impedance and its corresponding physical data from the infrared ray output circuit 15 to the main television unit 20. When the display selector key 47 of the keyboard 4 is turned on, the remote controller microcomputer 12 drives the infrared ray output circuit 15 to transmit a display selection signal to the main television unit 20 determining the type of display of the body fat. Moreover, when the sound keys 51 and 52 of the keyboard 4 are actuated, their sound adjusting signal is transmitted by the remote controller microcomputer 12 from the infrared ray output circuit 15 to the main television unit 20. In response to actuation of the power on key 50, the remote controller microcomputer 12 drives the infrared ray output circuit 15 to transmit its on/off signal to the main television unit 20.

Figure 5:
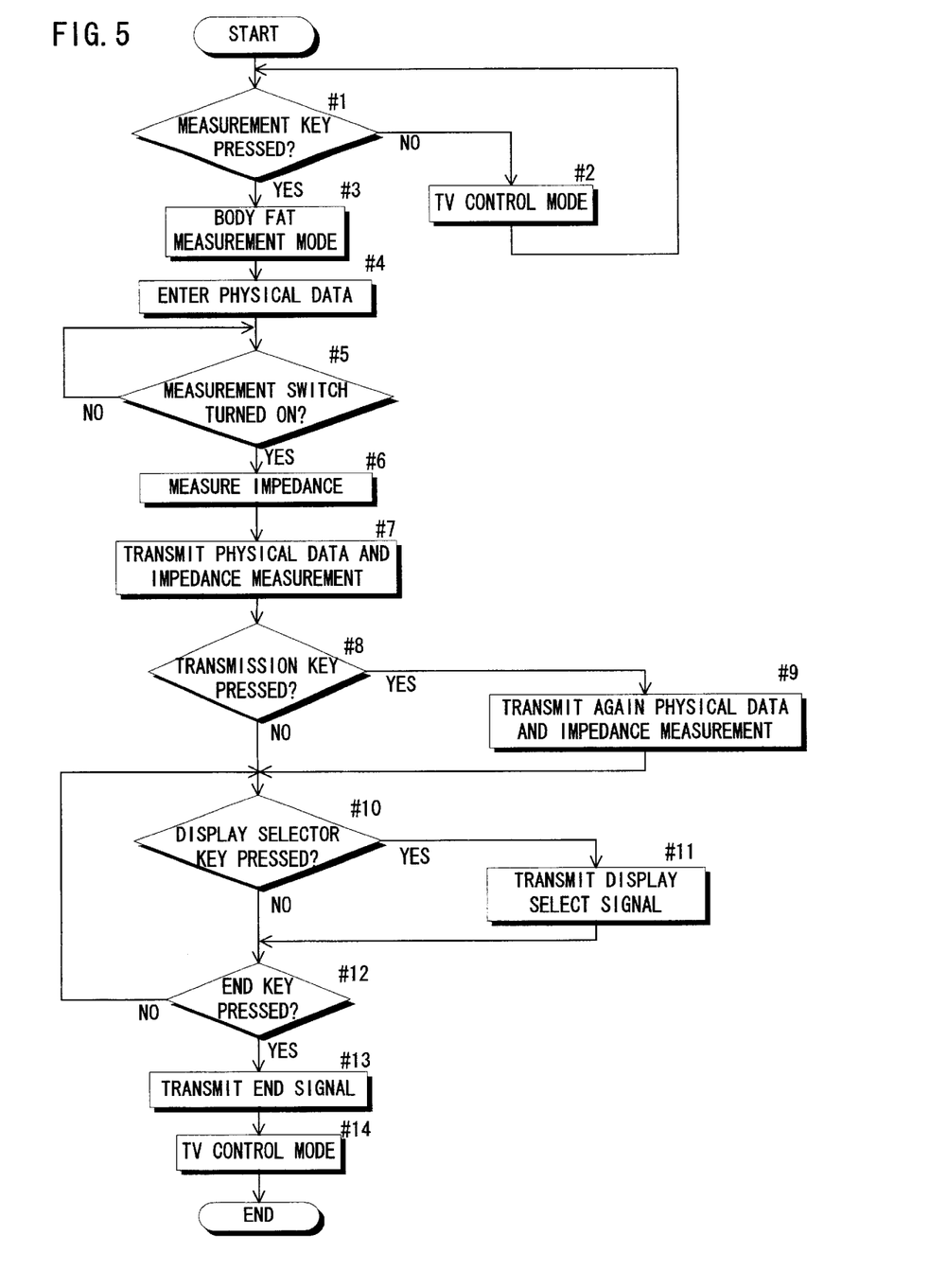
FIG. 5 is a flowchart showing a procedure of measuring the body fat in the remote controller for the television receiver.

A procedure of measuring the body fat with the remote controller 1 of the embodiment will now be explained referring to the flowchart of FIG. 5. The procedure starts with examining whether the measurement key 49 on the keyboard 4 is pressed down or not (#1). When the measurement key 49 is not pressed down (No at #1), the TV control mode for selecting a desired channel of the TV broadcasting service remains enabled (#2). When the measurement key 49 is pressed down (Yes at #1), the action is shifted to the body fat measurement mode for measuring the body fat (#3).

As the body fat measurement mode is selected at the step #3, the weight, the height, the sex, and the age of the user are entered using the weight entry key 41, the height entry key 42, the sex entry key 43, and the age entry key 44 in combination with the numerical keys 40 of the keyboard 4 (#4). The remote controller 1 saves those entries as the physical data in the RAM 14 and simultaneously displays the same on the liquid crystal display 5 for the user checkup.

When the measurement switch 6 of the remote controller 1 is turned on with the openable sections 3 opened and the electrodes 7 held directly by the user (yes at #5), the current electrodes 7a and 7b of the electrode section 7 is fed with a measurement current for measuring the impedance across the body of the user (#6). After the measurement of the impedance, the remote controller 1 reads out the physical data from the RAM 14 and transmits them in combination with the impedance as a body fat measurement signal to the main television unit 20 (#7). The body fat measurement signal also acts as an ON signal for switching the power source in the main television unit 20 on.

As the result, the body fat is calculated by the main television unit 20 from the impedance and the physical data including the weight, the height, the sex, and the age of the user and its calculation is then displayed. In case that the signal released at the step #7 fails to be received by the main television unit 20 (i.e. a calculation of the body fat is not displayed on the main television unit 20), the switching on of the transmission key 48 of the keyboard 4 by the user (Yes at #8) allows the remote controller 1 to transmit again the impedance and the physical data to the main television unit 20 (#9).

When the display selector key 47 of the keyboard 4 is pressed down (Yes at #10), the remote controller 1 transmits to the main television unit 20 a display select signal for determining the type of display of a measurement of the body fat (#11). Then, when the end key 46 of the keyboard 4 is pressed down (yes at #12), the remote controller 1 transmits an end signal for canceling the display of the measurement (#13) and its action returns back from the body fat measurement mode to the TV control mode (#14).

Figure 6:
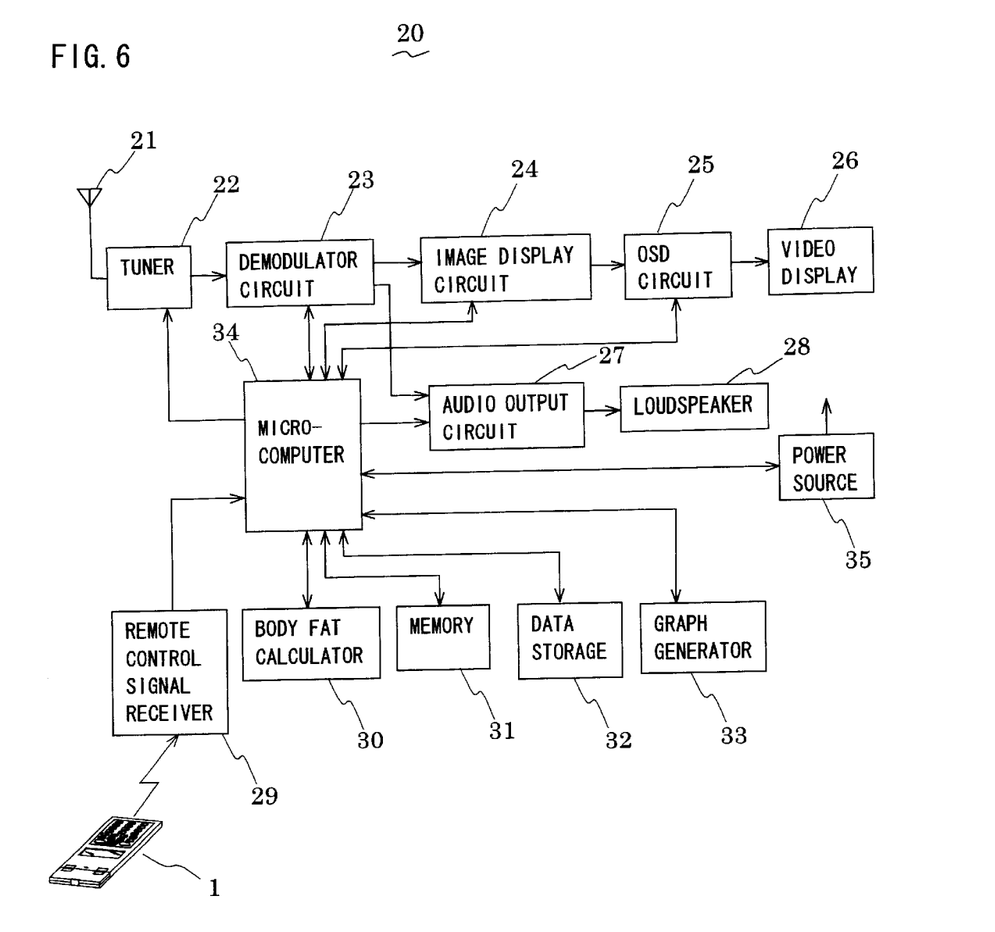
FIG. 6 is an electrical block diagram of a main television unit of the television receiver.

FIG. 6 is an electrical block diagram of the main television unit 20 in the body fat meter equipped television receiver 100 of the embodiment. The main television unit 20 comprises an antenna 21 for receiving TV broadcasting waves, a tuner 22, a demodulator circuit 23, an image display circuit 24, an OSD circuit 25, a video display 26, an audio output circuit 27, a loudspeaker 28, a remote control signal receiver 29, a body fat calculator 30, a memory 31, a data storage 32, a graph generator 33, a microcomputer 34, and a power source (power supply in the television receiver) 35 for supplying each of the above units with powers.

In the main television unit 20, the tuner 22 is controlled by the microcomputer 34 to tune the frequency of a desired channel of the TV broadcasting service for receiving a high-frequency TV signal at the channel with the antenna 21. The high-frequency TV signal is then demodulated by the demodulator circuit 23 and reconstructed to a video signal by the image display circuit 24 and to an audio signal by the audio output circuit 27. The video signal reconstructed by the image display circuit 24 is transferred via the OSD circuit 25 to the video display 26 where an image of the channel of the TV broadcasting service is displayed. The OSD circuit 25 is provided for displaying the number of the desired TV channel and a measurement of the body fat in OSD form on the screen of the video display 26. The audio signal reconstructed by the audio output circuit 27 is transferred to the loudspeaker 28 for emitting sounds of the channel of the TV broadcasting service.

The remote control signal receiver 29 is designed for receiving an infrared ray, signal from the remote controller 1. The body fat calculator 30 calculates the body fat of a user from the impedance across the body and the physical data including the weight, the height, the sex, and the age of the user which are carried on the body fat measurement signal and have been received by the remote control signal receiver 29. The memory 31 saves data of animation movie characters corresponding to the body fat rate determined by the body fat calculator 30. The data storage 32 is provided for storage of the body fat of each user calculated by the body fat calculator 30 and the physical data including the weight, the height, the sex, and the age of the user. The graph generator 33 yields a graphic representation of the body fat of each user in the form of a histogram or a bar graph which is based on the physical data saved in the data storage 32.

Figure 7:
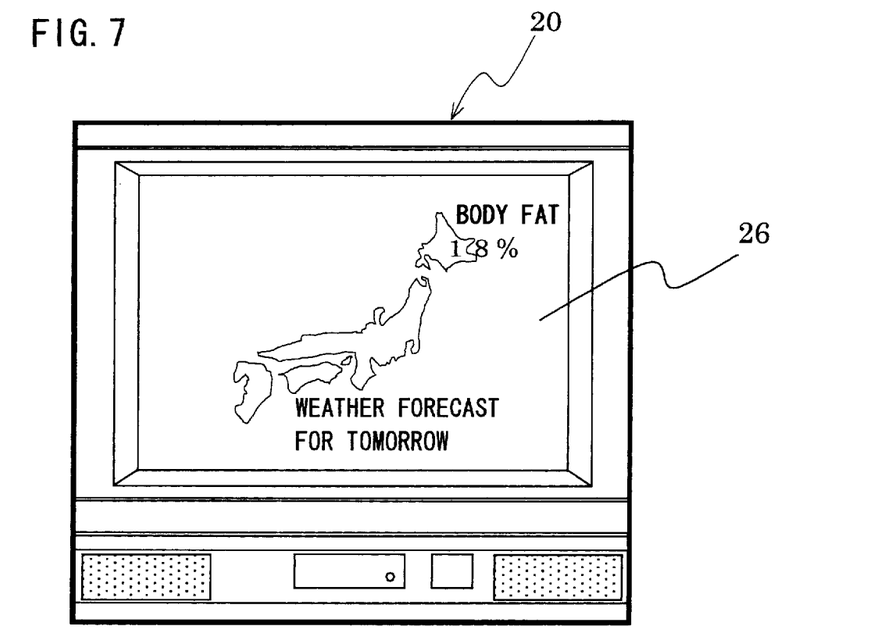
FIG. 7 illustrates one mode of a screen image on the television receiver showing a measurement of the body fat rate.

When a power on switch, not shown, in the main television unit 20 is turned on or when the on/off signal from the remote controller 1 is received by the remote control signal receiver 29, the microcomputer 34 switches the power source 35 on or off. In response to a select signal of a desired TV channel received by the remote control signal receiver 29 with the power source 35 remaining switched on, the microcomputer 34 drives the tuner 22 to tune the frequency of the desired channel of the TV broadcasting service and the video display 26 to display an image of the desired channel along with its corresponding sound emitted from the loudspeaker 28. When the remote control signal receiver 29 receives the body fat measurement signal with the power source 35 remaining switched on, the microcomputer 34 directs the body fat calculator 30 to calculate the body fat of the user and the video display 26 to display its calculation in an OSD form, for example, at an upper right region of the screen as shown in FIG. 7.

Figure 8:
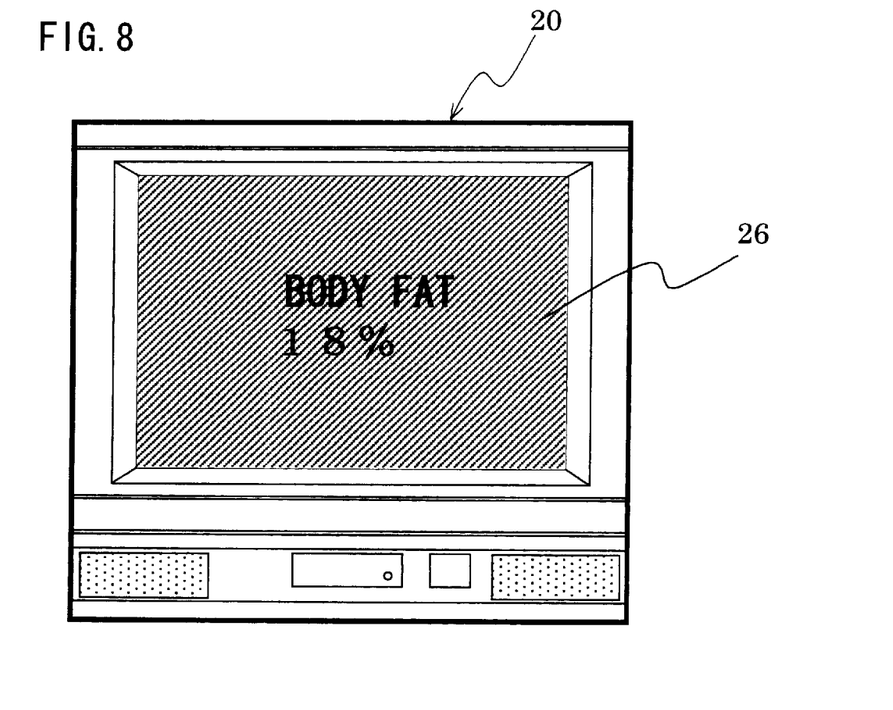
FIG. 8 illustrates another mode of the screen image on the television receiver showing the measurement of the body fat rate.

When receiving the body fat measurement signal at the remote control signal receiver 29 with the power source 35 remaining turned off, the microcomputer 34 switches the power source 35 on and then directs the video display 26 to display a blue back image and the body fat calculator 30 to calculate the body fat of the user. A calculation of the body fat may be displayed in an OSD form on the blue back image at the center of the screen of the video display 26 as shown in FIG. 8.

When receiving the display switch signal at the remote control signal receiver 29 after the body fat is displayed on the video display 26, the microcomputer 34 reads out a desired animation character corresponding to the body fat from the memory 31 for display in an OSD form on the video display 26 or reads out a past data of the body fat from the data storage 32 and directs the graph generator 33 to generate a histogram of the body fat from the past data and the current measurement of the body fat and the video display 26 to display the same in an OSD form. Upon receiving the end signal, the microcomputer 34 cancels the display of the body fat measurement or graph and proceeds the display of a desired channel of the television service.

Figure 9:
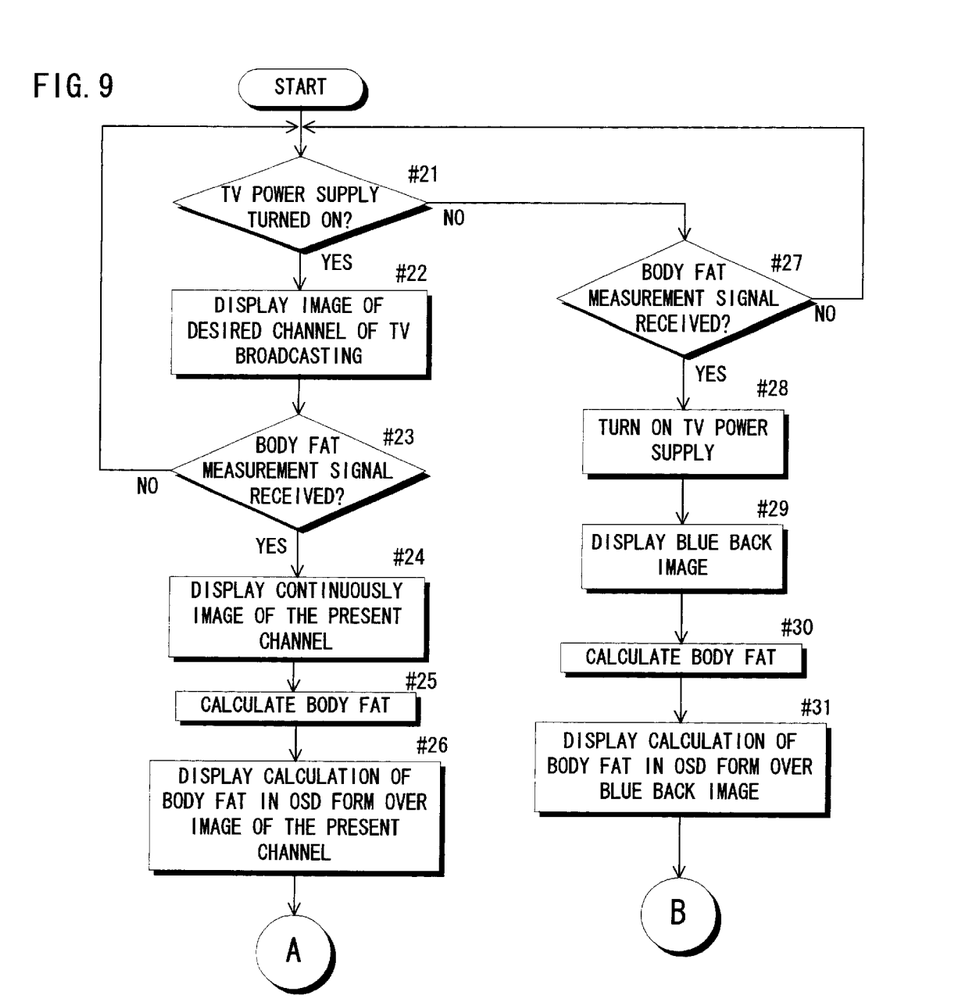
FIG. 9 is a flowchart showing a procedure of measuring the body fat in the main television unit of the television receiver.
Figure 10:
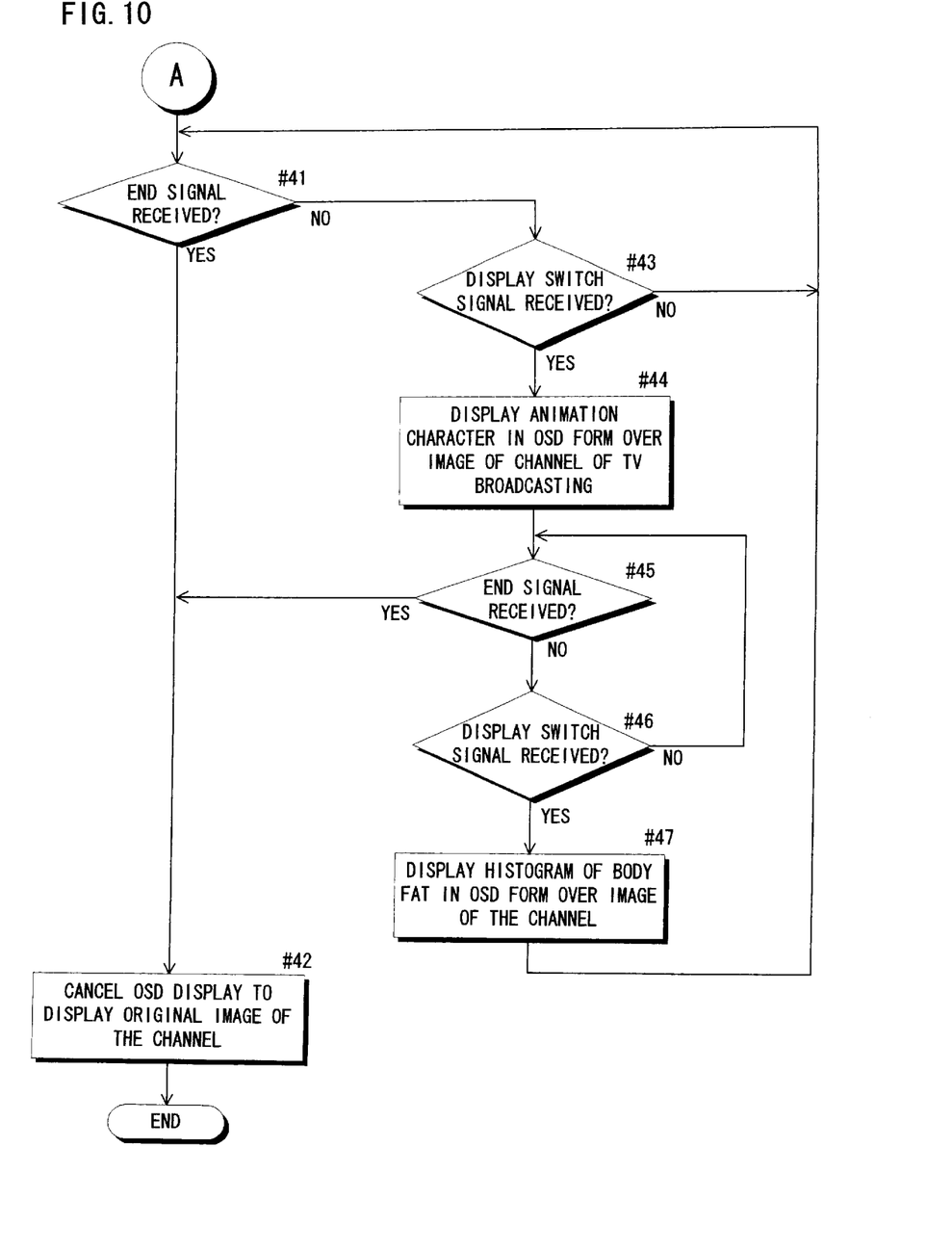
FIG. 10 is a flowchart showing a succeeding procedure of measuring the body fat in the main television unit of the television receiver.
Figure 11:
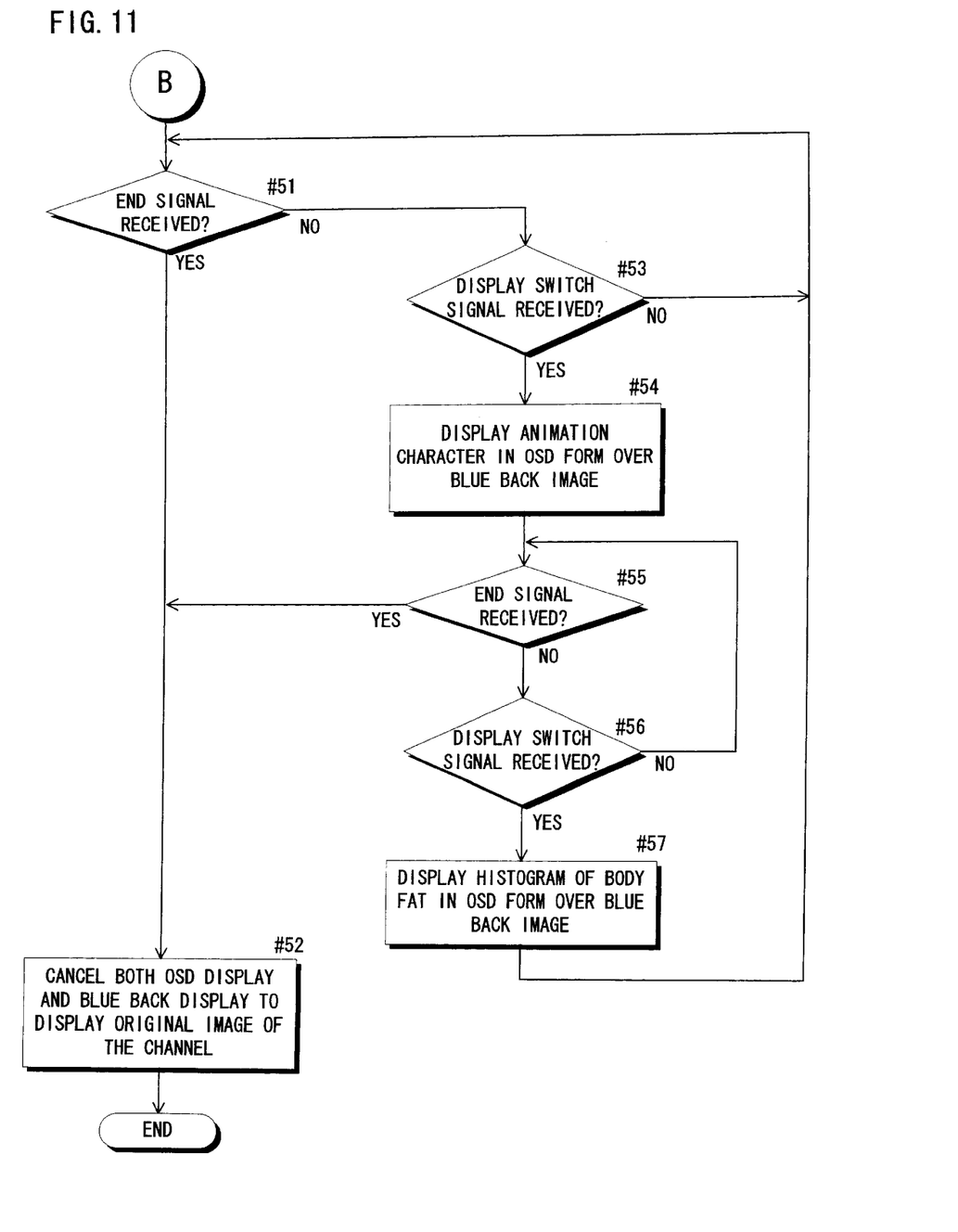
FIG. 11 is a flowchart showing an alternative succeeding procedure of measuring the body fat in the main television unit of the television receiver.

A procedure of calculating and displaying the body fat on the main television unit 20 will be explained referring to the flowcharts of FIGS. 9, 10, and 11. The procedure starts with the main television unit 20 examining whether or not the body fat measurement signal is received (#23) while a desired channel of the TV broadcasting service remains displayed on the video display 26 (#22) with the television power supply 35 turned on (Yes at #21). When the body fat measurement signal is received by the main television unit 20 with the television power supply 35 turned on (Yes at #23), the video display 26 is allowed to display continuously the image of the present channel of the TV broadcasting service (#24) and the body fat calculator 30 calculates the body fat of a desired user from the impedance across the body and the physical data including the weight, the height, the sex, and the age of the user which are carried on the body fat measurement signal (#25). A resultant calculation of the body fat is displayed in an OSD form over the image of the present channel of the TV broadcasting service on the video display 26 (#26).

Alternatively, when the television power supply 35 is turned off (No at #21), it is examined whether or not the main television unit 20 receives the body fat measurement signal (#27). When the body fat measurement signal is received by the main television unit 20 (Yes at #27), the power supply 35 in the main television unit 20 is switched on (#28) and a blue back image is displayed on the video display 26 (#29). Then, the body fat calculator 30 in the main television unit 20 calculates the body fat of a user from the impedance across the body and the physical data including the weight, the height, the sex, and the age of the user which are carried on the body fat measurement signal (#30) and its calculation is displayed in an OSD form over the blue back image on the screen of the video display 26 (#31).

When the end signal is received by the main television unit 20 with the body fat being displayed in an OSD form at #26 (Yes at #41), the OSD display of the body fat is canceled and the screen is returned back to the original image of the channel of the TV broadcasting service (#42). When the display switch signal is received (Yes at #43) with no reception of the end signal (No at #41), an animation character corresponding to the body fat is read out from the memory 31 and displayed in an OSD form over the image of the television service (#44) replacing the body fat measurement.

Then, when the end signal is received by the main television unit 20 (Yes at #45), the OSD display of the animation character is canceled and the screen is returned back to the original image of the channel of the TV broadcasting service (#42). When the display switch signal is received (Yes at #46) with no reception of the end signal (No at #45), a past data of the body fat measurement is read out from the data storage 32 and used together with the present measurement of the body fat by the graph generator 33 to generate a histogram of the body fat. The histogram of the body fat is then displayed in an OSD form on the screen replacing the animation character (#47). Then, the steps from #41 are repeated.

When the end signal is received by the main television unit 20 with the body fat being displayed in an OSD form at #31 (yes at #51), the OSD display of the body fat on the blue back image is canceled and the screen is returned back to the original image of the channel of the TV broadcasting service (#52). When the display switch signal is received (Yes at #53) with no reception of the end signal (No at #51), an animation character corresponding to the body fat is read out from the memory 31 and displayed in an OSD form over the blue back image (#54) replacing the body fat measurement.

Then, when the end signal is received by the main television unit 20 (Yes at #55), both the OSD display of the animation character and the blue back display are canceled and the screen is returned back to the original image of the channel of the TV broadcasting service (#52). When the display switch signal is received (Yes at #56) with no reception of the end signal (No at #55), a past data of the body fat measurement is read out from the data storage 32 and used together with the present measurement of the body fat by the graph generator 33 to generate a histogram of the body fat. The histogram of the body fat is then displayed in an OSD form on the screen replacing the animation character (#57). Then, the steps from #41 are repeated.

As described, the body fat meter equipped television receiver 100 of this embodiment has the remote controller 1 provided for measuring the impedance across the body and registering the physical data of a desired user with its action selecting the body fat measurement mode. Then, the body fat of the user is calculated from the impedance measurement and the physical data of the user in the main television unit 20 and displayed on its display 26. The measurement of the body fat can be carried out with the power supply 35 in the main television unit 20 remaining turned off. More specifically, the power supply 35 is turned on by the remote controller 1 starting the measurement of the body fat. A resultant measurement of the body fat is then displayed on the video display 26 of the main television unit 20.

Figure 12:
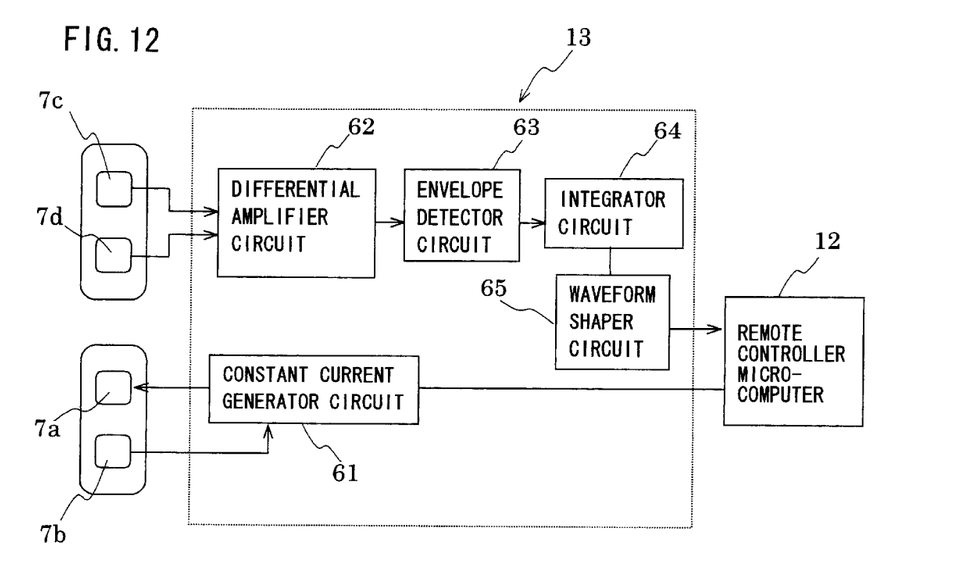
FIG. 12 is an electrical block diagram of an impedance measuring circuit in the remote controller for a body fat meter equipped television receiver showing a second embodiment of the present invention.

FIG. 12 is an electrical block diagram of an impedance measuring circuit 13 in a remote controller 1 showing a second embodiment of the present invention. The impedance measuring circuit 13 of this embodiment consists mainly of a constant current generator circuit 61, a differential amplifier circuit 62, an envelope detector circuit 63, an integrator circuit 64, and a waveform shaper circuit 65. The microcomputer 12 of the remote controller 1 has input ports thereof arranged in a digital mode for determining the high/low states of input signals.

The constant current generator circuit 61 is controlled by the remote controller microcomputer 12 for feeding a pair of current electrodes 7a and 7b with a small constant current at a high frequency of 50 kHz. The differential amplifier circuit 62 is provided for amplification of a difference between the voltage amplitude at the measurement electrode 7c and the voltage amplitude at the measurement electrode 7d. When the impedance across the body is high, the current running through the body will be low hence increasing a difference between the voltage amplitude at the measurement electrode 7c and the voltage amplitude at the measurement electrode 7d and allowing the differential amplifier circuit 62 to release an output wave of large amplitude. In reverse, when the impedance is low, the amplitude of an output wave from the differential amplifier circuit 62 will be small.

The envelope detector circuit 63 provides envelope detection of the amplitude of an output wave of the differential amplifier circuit 62. The integrator circuit 64 provides integration of an output of the envelope detector circuit 63. When the impedance across the body is high, the output of the integrator circuit 64 will increase. The waveform shaper circuit 65 is provided for converting the output of the integrator circuit 64 into a square waveform and more particularly shaping the waveform of an output of the integrator circuit 64 so that the interval from a rise to the following rise of the square waveform corresponds to the output of the integrator circuit 64. Accordingly, the interval from the rise to the following rise of the square waveform outputted from the waveform shaper circuit 65 is proportional to the impedance across the body.

The square waveform output of the waveform shaper circuit 65 is received as an output of the impedance measuring circuit 13 by the digital input port of the remote controller microcomputer 12. The remote controller microcomputer 12 reads the interval from the rise to the following rise of the square waveform to determine the impedance. The input ports of the remote controller microcomputer 12 are arranged in a digital mode for determining the high/low states of each signal. Since the interval from the rise to the following rise of the square waveform output of the impedance measuring circuit 13 is proportional to the amplitude of the impedance, it allows the remote controller microcomputer 12 to calculate the impedance across the body of the user. The other arrangements of this embodiment are identical to those of the first embodiment.

In the remote controller 1, the measurement of the impedance is implemented by the remote controller microcomputer 12 reading the interval from the rise to the following rise of the square waveform output of the impedance measuring circuit 13.

Figure 13:
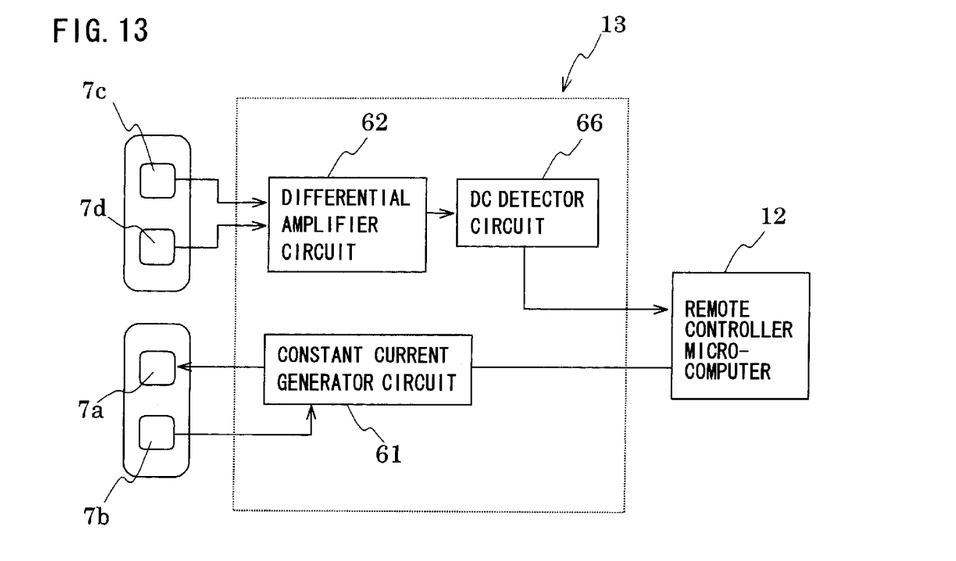
FIG. 13 is an electrical block diagram of an impedance measuring circuit in the remote controller for a body fat meter equipped television receiver showing a third embodiment of the present invention.

FIG. 13 is an electrical block diagram of an impedance measuring circuit 13 of a remote controller 1 showing a third embodiment of the present invention. The impedance measuring circuit 13 of this embodiment consists mainly of a constant current generator 61, a differential amplifier circuit 62, and a DC (Direct Current) detector circuit 66. The remote controller microcomputer 12 of this embodiment includes an A/D (analog-to-digital) converter and A/D ports for receiving analog signals.

The constant current generator 61 is controlled by the remote controller microcomputer 12 for feeding a pair of current electrodes 7a and 7b with a small constant current at a high frequency of 50 kHz. The differential amplifier circuit 62 is provided for amplification of a difference between the voltage amplitude at the measurement electrode 7c and the voltage amplitude at the measurement electrode 7d. When the impedance across the body is high, the measurement current running through the body will be low hence increasing a difference between the voltage amplitude at the measurement electrode 7c and the voltage amplitude at the measurement electrode 7d and allowing the differential amplifier circuit 62 to release an output wave of large amplitude. In reverse, when the impedance is low, the amplitude of an output wave from the differential amplifier circuit 62 will be small.

The DC detector circuit 66 is provided for DC detection of the amplitude of an output wave of the differential amplifier circuit 62 and its voltage output is proportional to the amplitude of the waveform output of the differential amplifier circuit 62. More particularly, the voltage output of the DC detector circuit 66 is proportional to the measurement of the impedance. The voltage output of the DC detector circuit 66 is received as an output of the impedance measuring circuit 13 by the A/D port of the remote controller microcomputer 12 where it is examined to determine the level of the impedance. Other arrangement of this embodiment are also identical to those of the previous embodiment.

Accordingly, the remote controller 1 allows the remote controller microcomputer 12 to read and examine the voltage output of the impedance measuring circuit 13 received at its A/D port for determining the level of the impedance across the body of the user.

The present invention is not limited to the above embodiments but may be implemented by appropriate modifications. For example, the body fat measurement signal carrying the physical data which has been registered and the impedance which has been measured by the action of the remote controller 1 may be transmitted from the remote controller 1 to the main television unit 20 only when the transmission key 48 of the remote controller 1 is switched on. Also, the body fat measurement signal carrying the physical data and the impedance may not serve as an ON signal for turning the main television unit 20 on. The ON signal for turning the main television unit 20 on may separately be provided and transmitted. Moreover, the ON signal for switching on the power supply 35 in the main television unit 20 may be fed to the main television unit 20 when the remote controller 1 is shifted to the body fat measurement mode by the measurement key 49 switched on. This allows the power supply 35 in the main television unit 20 to be turned on by the action of the measurement key 49 on the remote controller 1.

It may also be possible according to any of the embodiments that the body fat is calculated from the impedance and the physical data by the remote controller 1, transmitted from the remote controller 1 to the main television unit 20, and displayed on the display of the main television unit 20. In that case, the power supply 35 of the main television unit 20 may be switched on upon receiving a signal of the body fat from the remote controller 1.

The remote controller 1 may be modified for selecting between the image of the TV channel and the blue back image and displaying a measurement of the body fat over the selected image. The blue back image may appear as a PIP window in the screen where the measurement of the body fat is superimposed. Also, the measurement of the body fat may be displayed on any background image as well as the blue back image or TV channel image. The remote controller microcomputer 12 may be replaced by a commercial microcomputer. This application has a priority right based on a couple of the utility model applications No. 2001-7046 filed on Oct. 29, 2001 and No. 2001-7292 filed on Nov. 7, 2001 of which all the teachings shall be referenced and covered by this application.

What is claimed is:

1. A remote controller for a television with a function of measuring a body fat having a transmitter which transmits a select signal for selecting a desired receiving/recording channel of television broadcasting to a television receiver and a control section which controls actions of each section of the remote controller, comprising:

a physical data setting section which is operated by a user for registering physical data including a weight and a height of the user;

an electrode section including a pair of current electrodes which feed a current across the body of the user through direct contact with the body and a pair of measurement electrodes which detect an electric signal generated by the current being fed across the body of the user; and an impedance measuring circuit which feeds the current between the current electrodes of the electrode section and measures an impedance across the body of the user to determine a body fat of the user from the electric signal detected by the measurement electrodes, wherein the transmitter is controlled by the control section to transmit to the television receiver a body fat measurement signal which carries the physical data registered by the physical data setting section and the impedance measured by the impedance measuring circuit so that the body fat of the user can be calculated in the television receiver.

2. A remote controller for a television with a function of measuring a body fat according to claim 1, further comprising a body fat measurement key for starting a body fat measurement mode to measure the body fat of the user, wherein the body fat measurement mode allows an ON signal for turning on a power supply in the television receiver to be transmitted together with the body fat measurement signal from the transmitter to the television receiver.

3. A remote controller for a television with a function of measuring a body fat according to claim 2, wherein the ON signal for turning on the power supply in the television receiver is transmitted to the television receiver when the body fat measurement key is switched on.

4. A remote controller for a television with a function of measuring a body fat according to claim 2, wherein the body fat measurement mode allows the ON signal for turning on the power supply in the television receiver to be automatically transmitted to the television receiver when the impedance across the body of the user has been measured by the impedance measuring circuit.

5. A remote controller for a television with a function of measuring a body fat according to claim 2, further comprising a transmission key for starting the transmission of the body fat measurement signal to the television receiver, wherein when the transmission key is switched on in the body fat measurement mode after the completion of the measurement of the impedance across the body, an ON signal for turning on the power supply in the television receiver is transmitted to the television receiver.

6. A remote controller for a television with a function of measuring a body fat according to claim 2, further comprising a transmission key for starting the transmission of the body fat measurement signal to the television receiver, wherein when the body fat measurement key is switched on, an ON signal for turning on the power supply in the television receiver is transmitted to the television receiver and when the transmission key is switched on after the completion of the measurement of the impedance across the body, the body fat measurement signal is transmitted to the television receiver.

7. A remote controller for a television with a function of measuring a body fat according to claim 2, further comprising a transmission key for starting the transmission of the body fat measurement signal to the television receiver, wherein when the transmission key is switched on in the body fat measurement mode after the completion of the measurement of the impedance across the body, an ON signal for turning on the power supply in the television receiver is transmitted together with the body fat measurement signal to the television receiver.

8. A remote controller for a television with a function of measuring a body fat according to claim 1, wherein the impedance measuring circuit comprises a constant current generator circuit for feeding the two current electrodes with a constant current, a differential amplifier circuit for amplifying a difference in voltage between the two measurement electrodes, an envelope detector circuit for detecting the envelope of an output of the differential amplifier circuit, an integrator circuit for integrating an output of the envelope detector circuit, and a waveform shaper circuit for shaping the waveform of an output of the integrator circuit into a square wave, so that the impedance across the body can be determined by the control section examining an interval from a rise to a following rise of the square wave released from the waveform shaper circuit.

9. A remote controller for a television with a function of measuring a body fat according to claim 1, wherein the impedance measuring circuit comprises a constant current generator circuit for feeding the two current electrodes with a constant current, a differential amplifier circuit for amplifying a difference in voltage between the two measurement electrodes, and a DC detector circuit for DC detecting an output of the differential amplifier circuit, so that the impedance across the body can be determined by the control section in the remote controller examining a voltage of an output of the DC detector circuit.

10. A television receiver having a function of measuring a body fat, comprising:

a remote controller having a transmitter which transmits a select signal for selecting a desired receiving/ recording channel of television broadcasting to a television receiver and a control section which controls actions of each section of the remote controller; and a main television unit having a remote control signal receiver which receives the select signal from the remote controller and an video display which displays an image of the desired channel of the television broadcasting determined by the select signal received at the remote control signal receiver, the remote controller including, a physical data setting section which is operated by a user for registering physical data including a weight and a height of the user;

an electrode section including a pair of current electrodes which feed a current across the body of the user through direct contact with the body and a pair of measurement electrodes which detect an electric signal generated by the current being fed across the body of the user; and an impedance measuring circuit which feeds the current between the current electrodes of the electrode section and measures an impedance across the body of the user to determine a body fat of the user from the electric signal detected by the measurement electrodes, wherein the transmitter is controlled by the control section to transmit to the television receiver a body fat measurement signal which carries the physical data registered by the physical data setting section and the impedance measured by the impedance measuring circuit so that the body fat of the user can be calculated in the television receiver, the main television unit including, a body fat calculator which calculates the body fat of the user from the impedance and the physical data which are carried in the body fat measurement signal received at the remote control signal receiver, wherein a resultant calculation of the body fat of the user determined by the body fat calculator is displayed on the video display of the television receiver.

11. A television receiver having a function of measuring a body fat according to claim 10, wherein the remote controller includes a body fat measurement key for starting a body fat measurement mode to measure the body fat of the user and the body fat measurement mode allows an ON signal for turning on a power supply in the main television unit to be transmitted together with the body fat measurement signal from the transmitter section to the main television unit, and when receiving the ON signal at the remote control signal receiver, the power supply in the main television unit remaining turned off can be turned on.

12. A television receiver having a function of measuring a body fat according to claim 11, wherein when the power supply is turned on by the reception of the ON signal, the main television unit displays a resultant calculation of the body fat of the user in an on-screen-display (OSD) form over a blue back screen on the video display.

13. A television receiver having a function of measuring a body fat according to claim 11, wherein when the power supply remains turned on at the reception of the ON signal, the main television unit displays a resultant calculation of the body fat of the user in an OSD form over an image of the television broadcasting on the video display.

14. A television receiver having a function of measuring a body fat according to claim 11, wherein when the power supply is turned on by the reception of the ON signal, the main television unit displays a resultant calculation of the body fat of the user in an OSD form over a blue back screen on the video display, or when the power supply remains turned on at the reception of the ON signal, the main television unit displays a resultant calculation of the body fat of the user in an OSD form over an image of the television broadcasting on the video display.

* * * * *